(12) United States Patent
Tam

(10) Patent No.: US 10,835,745 B2
(45) Date of Patent: Nov. 17, 2020

(54) NON-INVASIVE DEVICE AND METHOD FOR STIMULATING VULVAR TISSUES AND PELVIC FLOOR MUSCLES FOR TREATING AND IMPROVING DYSFUNCTION OR DISORDERS AND PROBE UNIT USED THEREFOR

(71) Applicant: Pui Ling Tam, Kowloon (HK)

(72) Inventor: Pui Ling Tam, Kowloon (HK)

(*) Notice: Subject to any disclaimer, the term of this patent is extended or adjusted under 35 U.S.C. 154(b) by 234 days.

(21) Appl. No.: 15/679,423

(22) Filed: Aug. 17, 2017

(65) Prior Publication Data

US 2018/0050201 A1 Feb. 22, 2018

Related U.S. Application Data

(60) Provisional application No. 62/376,092, filed on Aug. 17, 2016.

(51) Int. Cl.
*A61N 1/36* (2006.01)
*A61N 1/04* (2006.01)
*A61N 1/05* (2006.01)

(52) U.S. Cl.
CPC ....... *A61N 1/36007* (2013.01); *A61N 1/0452* (2013.01); *A61N 1/36014* (2013.01);
(Continued)

(58) Field of Classification Search
None
See application file for complete search history.

(56) References Cited

U.S. PATENT DOCUMENTS 3,640,284 A * 2/1972 De Langis ........... A61B 5/1073
607/71
3,918,459 A * 11/1975 Horn .................... A61N 1/20
607/64

(Continued)

FOREIGN PATENT DOCUMENTS

| CN | 102300602 | 12/2011 |
| CN | 103096973 | 5/2013 |
| CN | 103285511 | 9/2013 |

OTHER PUBLICATIONS

Notification of Transmittal of the International Search Report and the Written Opinion of the International Searching Authority . . . , from PCT/CN2017/097835, dated Nov. 22, 2017.

(Continued)

*Primary Examiner* — Kennedy Schaetzle
(74) *Attorney, Agent, or Firm* — Browdy and Neimark, P.L.L.C.

(57) ABSTRACT

The present invention relates to a non-invasive device and method for treating and improving dysfunction or disorders associated with pelvic floor. In one advantageous form, the non-invasive device comprising a generator configured to generate a current with a predetermined intensity of milliampere at a desirable frequency; at least one electrical stimulation applicator comprising a probe unit configured to transmit the current to a target body surface of vulvar tissues and/or pelvic floor muscle for application of an electrical stimulation; wherein the probe unit comprises a negative electrode and at least one positive electrode and the probe unit is shaped for positioning on the target body surface of the vulvar tissues and/or the pelvic floor muscle.

19 Claims, 15 Drawing Sheets

(52) U.S. Cl.
CPC ........ *A61N 1/36034* (2017.08); *A61N 1/0476* (2013.01); *A61N 1/0512* (2013.01); *A61N 1/0521* (2013.01); *A61N 1/36003* (2013.01)

(56) References Cited

U.S. PATENT DOCUMENTS

| | | | | |
|---|---|---|---|---|
| 4,363,324 | A * | 12/1982 | Kusserow | H02H 3/10 607/64 |
| 4,411,648 | A * | 10/1983 | Davis | A61N 1/306 604/21 |
| 4,580,578 | A | 4/1986 | Barsom | |
| 4,688,575 | A * | 8/1987 | DuVall | A61N 1/36007 607/41 |
| 5,199,442 | A * | 4/1993 | Seager | A61N 1/0512 600/547 |
| 9,149,634 | B2 * | 10/2015 | Lee | A61N 1/36014 |
| 9,320,893 | B2 * | 4/2016 | Hagege | A61N 1/36007 |
| 9,623,231 | B2 * | 4/2017 | Kolb | A61N 1/0452 |
| 9,821,163 | B2 * | 11/2017 | Fraga Da Silva | A61N 1/36107 |
| 2003/0083590 | A1 * | 5/2003 | Hochman | A61B 5/0002 600/549 |
| 2009/0030266 | A1 * | 1/2009 | Treanor | A61N 1/0524 600/30 |
| 2009/0076565 | A1 * | 3/2009 | Surwit | A61N 1/36007 607/41 |
| 2015/0352357 | A1 * | 12/2015 | Wei | A61N 1/0456 604/385.03 |
| 2016/0114154 | A1 * | 4/2016 | Bozzarelli | A61N 1/0524 607/41 |
| 2016/0235981 | A1 * | 8/2016 | Southwell | A61N 1/22 |
| 2017/0182320 | A1 * | 6/2017 | Kolb | A61N 1/36007 |
| 2017/0216576 | A1 * | 8/2017 | Gregson | A61N 1/36007 |
| 2017/0368329 | A1 * | 12/2017 | Tyler | A61N 1/0472 |

OTHER PUBLICATIONS

International Search Report from PCT/CN2017/097835, dated Nov. 22, 2017.
Written Opinion from PCT/CN2017/097835, dated Nov. 22, 2017.

* cited by examiner

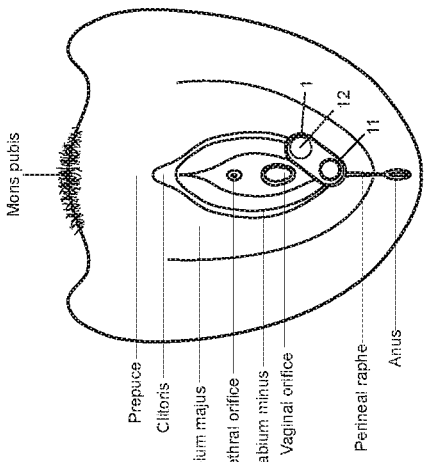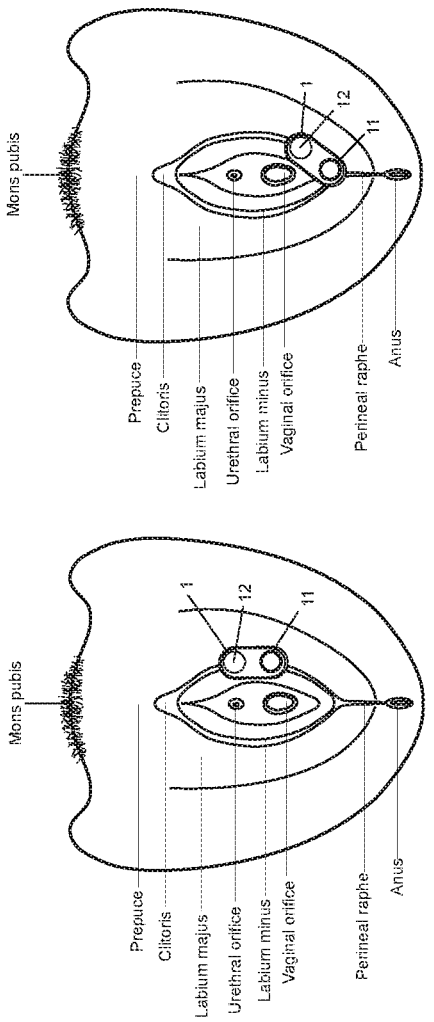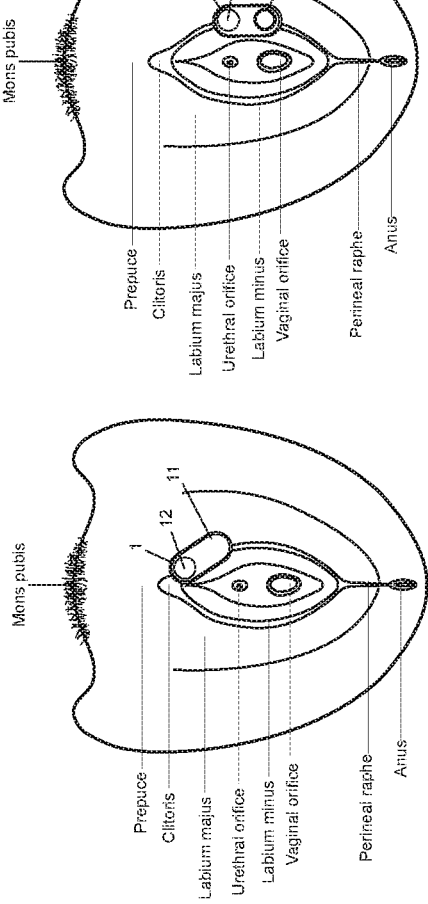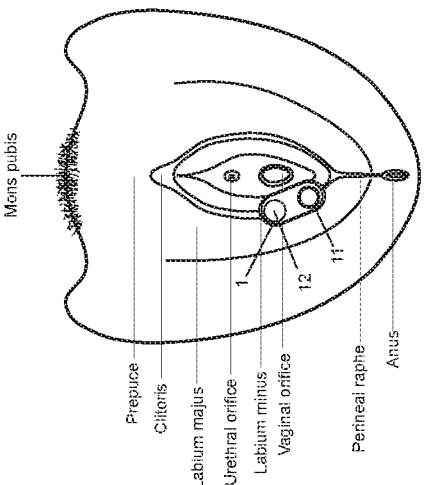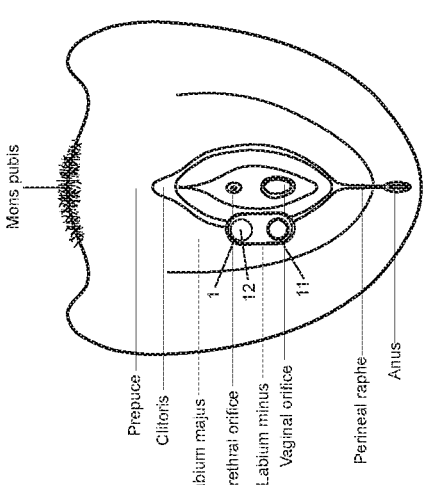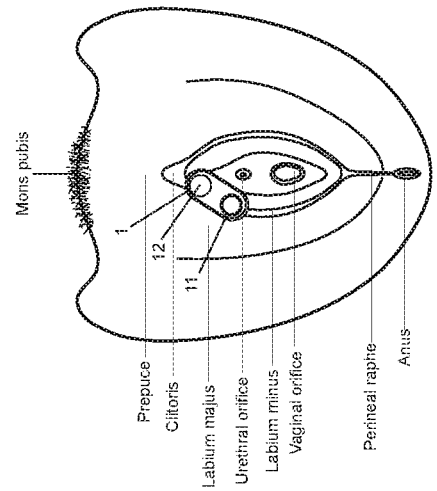

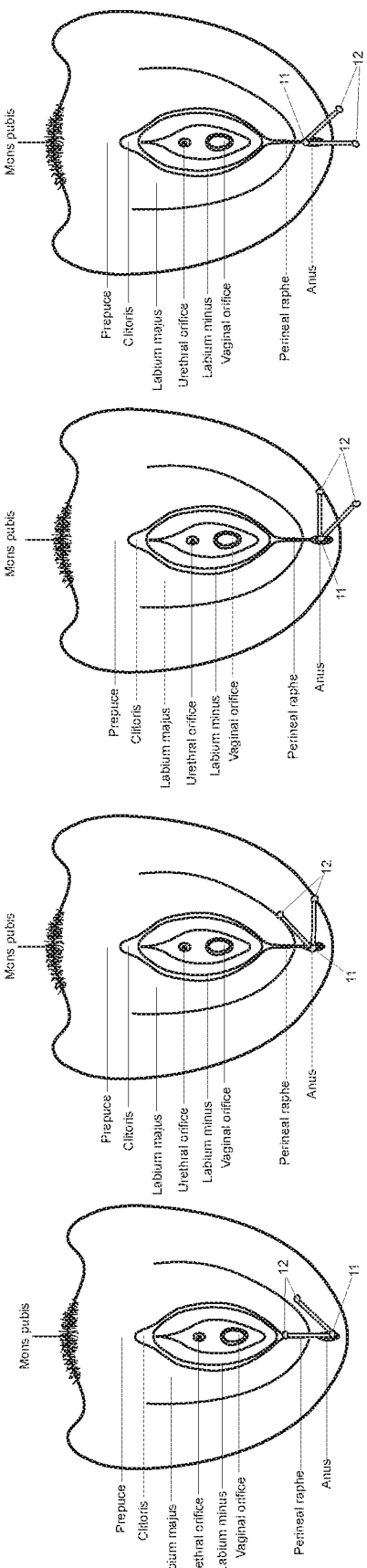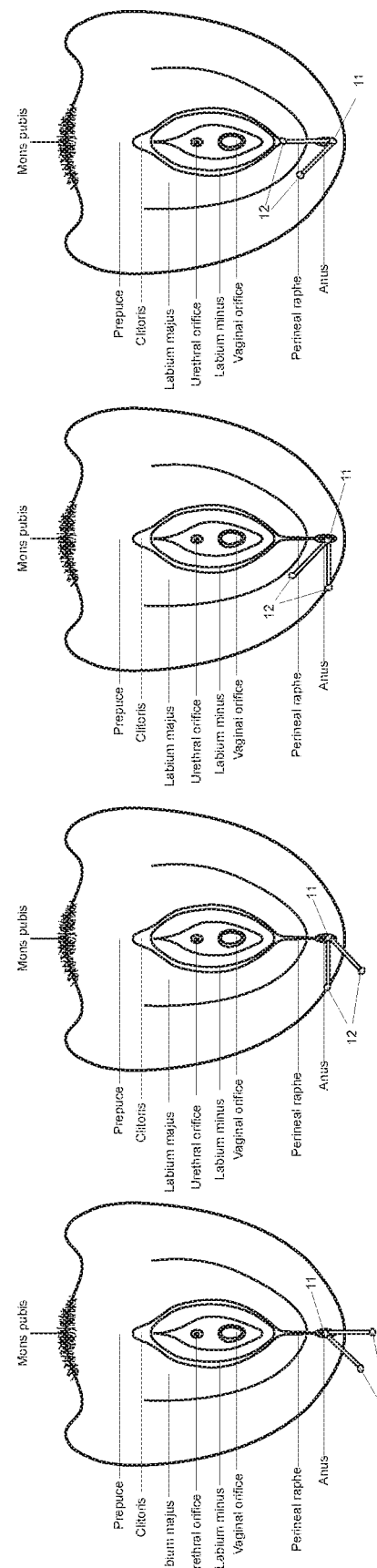

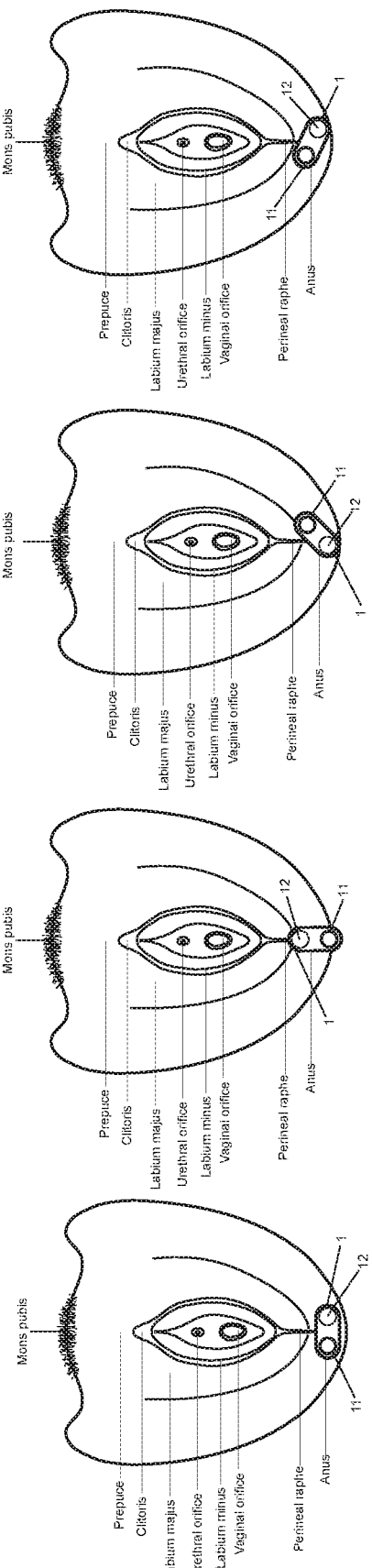
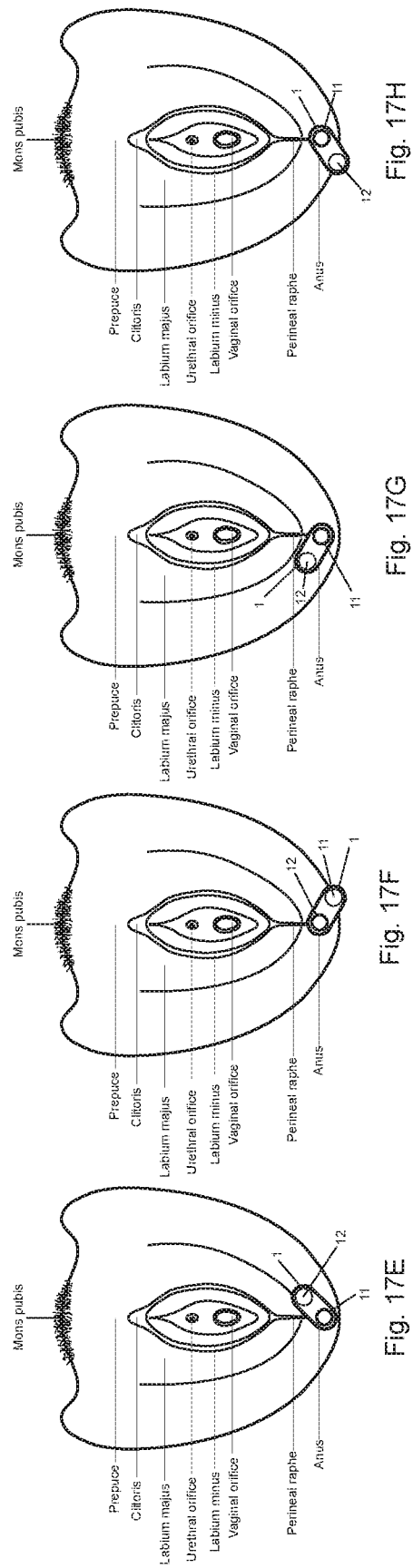

NON-INVASIVE DEVICE AND METHOD FOR STIMULATING VULVAR TISSUES AND PELVIC FLOOR MUSCLES FOR TREATING AND IMPROVING DYSFUNCTION OR DISORDERS AND PROBE UNIT USED THEREFOR

CROSS-REFERENCE TO RELATED APPLICATION

This application claims the benefit of U.S. Provisional Application No. 62/376,092, filed Aug. 17, 2016. The contents of the aforementioned application are hereby incorporated by reference in its entirety.

TECHNICAL FIELD OF THE INVENTION

This invention relates generally to the technical field of medical devices, and more particularly, to a method and apparatus for stimulating the vulvar tissues and pelvic floor muscle for treating and improving dysfunction or disorders associated with pelvic floor.

BACKGROUND OF THE INVENTION

Pelvic floor muscles are the layer of muscles that support the pelvic organs and span the bottom of the pelvis. They play an important role in maintaining normal physiological position and achieving normal physiological function of pelvic organs including the bladder, uterus (women), prostate (men), and rectum. Pelvic floor muscles are also important for sexual function in both men and women. In women, voluntary contractions of the pelvic floor contribute to sexual sensation and arousal. However, pregnancy, childbirth, pelvic surgery, obesity, strenuous exercise and other factors may lead to the weakening of the pelvic floor muscles and affect their ability to be activated, thereby causing urinary incontinence, constipation, pelvic pain, pain for women during intercourse as well as other dysfunction and disorders related to pelvic floor. In recent years, evidence has emerged that a large majority of dysfunction or disorders associated with pelvic floor is related to muscle dysfunction and/or muscle related pain of pelvic floor. These conditions can usually be improved by restoring the muscle strength of the patients' pelvic floor muscles. Conventionally, this may be realized through physical training or electrical stimulation of the muscles One such method is the use of neuromuscular electrical stimulation (NMES) which includes applying neuromuscular stimulation in the form of repeated applications of electrical pulses to the pelvic floor muscles to cause the muscles to repeatedly contract and relax. However, previous disclosed neuromuscular electrical stimulation may include applying a high electrical pulse which may lead to an uncomfortable sensation and may even be painful to the patient. Further, conventional method in the prior art required the electrodes to be applied intrarectally or intravaginally. Thus, the technique are considered invasive to the patient. The invasive electrodes may cause injury to the body lumen and lead to further discomfort.

There is therefore a need to develop a non-invasive device and method for treating and improving dysfunction or disorders associated with pelvic floor which has little to none painful sensation but yet effective.

SUMMARY OF THE INVENTION

An object of the present invention is to provide an effective, non-invasive, safe and hygienic method and device for stimulating the vulvar tissues and pelvic floor muscle for treating dysfunction or disorders associated with pelvic floor muscle so as to overcome the shortcomings of the prior art. The non-invasive device is particularly devised for vulva and pelvic floor and for use by women, which includes an electrical stimulation applicator for supplying an electrical stimulation to muscular, tendinous and connective tissues in the vulva and pelvic floor in non-invasive manner, so as to make these tissue structure more elastic, firmer and stronger.

Another function of the non-invasive device is to retrain a flabby pelvic floor musculature, e.g. caused by childbirth, or for ordinary maintenance training, and may also contribute to contraction of the above-mentioned structures.

Another object of the present invention is to provide a probe unit for stimulating the muscles of a patient wherein the probe unit in contact with the patient's body surface are disposable after use to prevent cross contamination between patients.

Another object of the present invention is to provide a disposable probe unit for stimulating the muscles of a subject wherein the disposable probe unit has a simple structure which is easy and economical for mass production.

To attain the aforesaid objects, one aspect of the present invention is to provide a non-invasive device for stimulating vulvar tissues and/or pelvic floor muscles for treating and improving dysfunction or disorders associated with the pelvic floor, said device comprises: a generator configured to generate a current with a predetermined intensity of milliamperes at a desirable frequency; said generator comprising a control unit configured to control the generation of the current; the device further comprises at least one electrical stimulation applicator comprising a distal end electrically connected to the generator and configured to receive the current generated by the generator, and a proximal end electrically connected to a probe unit configured to transmit the current to a target body surface of the vulvar tissues and/or the pelvic floor muscle for application of an electrical stimulation; wherein the probe unit comprises a negative electrode and at least one positive electrode and the probe unit is shaped for positioning on the target body surface of the vulvar tissues and the pelvic floor muscle; wherein the control unit of the generator is programed to deliver at least one treatment cycle consisting of
- a contraction phase where the electrical stimulation is applied to the target vulvar tissues and/or the target pelvic floor muscle for a first period of time; and
- a relaxation phase where no electrical stimulation is applied to the target vulvar tissues and/or the target pelvic floor muscle for a second period of time.

In one embodiment of the present invention, the control unit of the generator comprises a frequency adjustment module for adjusting the frequency of the generated current, and a timer logic module configured to control a length of the contraction phase and a length of the relaxation phase.

In one embodiment of the present invention, the frequency adjustment module comprises a frequency circuit and a frequency selector configured to select the frequency of the current.

In one embodiment of the present invention, the control unit of the generator further comprises a protection logic module configured to switch off the device if any one of the frequency or the intensity of the generated current exceeds a predefined safety threshold.

In one embodiment of the present invention, the intensity of the electrical stimulation at the contraction phase is in the range of 1.0-5.0 mA, preferably in the range of 1.0-4.0 mA;

and the frequency of the electrical stimulation at the contraction phase is in the range of 70-150 Hz and preferably in the range of 80-120 Hz, and wherein the contraction phase lasts for 2 to 5 seconds, preferably 3 to 5 seconds and more preferably 4 seconds.

In another embodiment of the present invention, the electrical stimulation at the contraction phase has a pulse duration in the range of 50 to 200 µs and preferably in the range of 100 to180 µs.

In yet another embodiment of the present invention, the relaxation phase lasts for 2 to 7 seconds, preferably 5 to 7 seconds, and more preferably 6 seconds.

In yet another embodiment of the present invention, the probe unit is a disposable probe unit detachably attached to the proximal end of the electrical stimulation applicator.

In yet another embodiment of the present invention, wherein the probe unit comprises 1 to 8 positive electrodes.

In yet another embodiment of the present invention, the probe unit is shaped for positioning on or around the body surface of the following selected from a group consisting of labia majora and labia minora of vulva, clitoris of vulva, external urethral sphincter muscle of vulva, vaginal orifice, perineum, and anus for stimulating the pelvic floor muscle in the region.

In yet another embodiment of the present invention, the probe unit is configured to have a rectangular shape and includes one negative electrode and one positive electrode opposite with each other in a length direction of the rectangular shape, and preferably the probe unit have a rectangular shape with rounded edges.

In yet another embodiment of the present invention, the probe unit comprises a plurality of ribs extending radially from the negative electrode, wherein one positive electrode is located at a free end of each of the ribs.

In yet another embodiment of the present invention, the probe unit is configured to have a "V" shape with two ribs extending radially from the negative electrode and the probe unit comprises two positive electrodes with each located at a free end of each of the ribs.

In yet another embodiment of the present invention, the probe unit further comprises a handle connecting the two ribs.

In yet another embodiment of the present invention, the probe unit comprises four equally spaced ribs extending radially from the negative electrode and the probe unit comprises four positive electrodes with each located at a free end of each of the ribs.

In yet another embodiment of the present invention, the probe unit comprises eight equally spaced ribs extending radially from the negative electrode and the probe unit comprises eight positive electrodes with each located at a free end of each of the ribs.

In yet another embodiment of the present invention, the probe unit further comprises an anti-skid member on the surface of the probe unit in contact with the target body surface.

According to a second aspect of the present invention there is provided a method for application of electrical stimulation to stimulate vulvar tissues and/or pelvic floor muscles for treating dysfunction or disorders associated with the pelvic floor, the method comprising the steps of:
placing at least one electrical stimulation applicator comprising a probe unit externally and directly onto a target body surface where the vulvar tissues and the pelvic floor muscles are located, wherein the probe unit which is in contact with the target body surface comprises one negative electrode and at least one positive electrode; generating a current with a predetermined intensity of milliampere and at a desirable frequency by a generator and providing the current to the probe unit for application of the electrical stimulation to the vulvar tissues and/or the pelvic floor muscle; wherein the method further comprises at least one treatment cycle consisting of a contraction phase where the electrical stimulation is applied to the target vulvar tissues and/or the target pelvic floor muscle for a first period of time and a relaxation phase where no electrical stimulation is applied to the target vulvar tissues and/or the target pelvic floor muscle for a second period of time.

In one embodiment of the present invention, the probe unit is placed directly on or around the body surface of the following selected from a group consisting of labia majora and labia minora of vulva, clitoris of vulva, external urethral sphincter muscle of vulva, vaginal orifice, perineum, and anus.

According to a third aspect of the present invention there is provided a disposable probe unit for application of electrical stimulation on vulvar tissues and/or pelvic floor muscles, the probe unit is in electrical connection with a generator for generating a current, wherein the probe unit comprises a negative electrode and at least one positive electrode and the probe unit is shaped for positioning on a target body surface where the patient's vulvar tissues and/or pelvic floor muscles are located.

To have a better understanding of the invention, reference is made to the following detailed description of the invention and embodiments thereof in conjunction with the accompanying drawings.

BRIEF DESCRIPTION OF THE DRAWINGS

The accompanying drawings herein are provided to enable a better understanding of the present invention, which constitute a part of the present application and shall not be construed as limiting the present invention, wherein:

FIG. 9A-9F show ways for positioning the probe unit of FIG. 2 on a target body surface for improving the firmness and elasticity of labia minora.

FIG. 16A-16H show ways for positioning the probe unit of FIG. 3 on a target body surface for improving the strength, blood circulation and firmness of external anal sphincter muscle.

FIG. 17A-17H show ways for positioning the probe unit of FIG. 2 on a target body surface for improving the strength, blood circulation and firmness of external anal sphincter muscle.

DETAILED DESCRIPTION OF THE DRAWINGS

For the sake of a better and clearer understanding of the objects, technical solutions, and advantages of the invention, embodiments of the present invention will be illustrated in more details by way of example with reference to the accompanying drawings.

Generally described, the present invention relates to devices and methods for stimulating the vulva tissues and pelvic floor muscles for treating and improving dysfunction or disorders associated with pelvic floor. Dysfunction or disorders associated with pelvic floor, which are characterized by weakness of or injury to the ligaments, connective tissue, and muscles of the pelvis, include, but not limited to, urinary incontinence, fecal incontinence, pelvic organ prolapse, sensory and emptying abnormalities of the lower urinary tract, defecatory dysfunction, and sexual dysfunction. It should be understood that the devices and methods described herein may also be used to treat other conditions of the body related to muscle weakness or injury.

The present invention relates to a non-invasive device for stimulating vulvar tissues and pelvic floor muscles for treating and improving dysfunction or disorders associated with the pelvic floor, said device comprises a generator configured to generate a current in milliampere and at a desirable frequency. The generator may comprise a control unit for controlling the generation of the current and transmitting the current to the electrical stimulation applicator. The control unit may comprise modules for adjusting the frequency, the intensity, the pulse duration of the current which is delivered to the electrical stimulation applicator and applied to the target muscle site of the subject. It will be appreciated that, depending on the particular application, the current generated by the generator can be a Faradic current, a direct current (DC) or an alternate current (AC), preferably the Faradic current for the invention. Further, the control unit is programmed to deliver at least one treatment cycle consisting of a contraction phase where the electrical stimulation is applied to the target vulvar tissues and/or the target pelvic floor muscle for a first period of time; and a relaxation phase where no electrical stimulation is applied to the target vulvar tissues and/or the target pelvic floor muscle for a second period of time. In particular, the contraction phase of the treatment cycle may last for 2 to 5 seconds, preferably 3-5 seconds, and more preferably 4 seconds. Whereas, the relaxation phase of the treatment cycle may last for 2 to 7 seconds, preferably 5 to 7 seconds, and more preferably 6 seconds.

Figure 1:
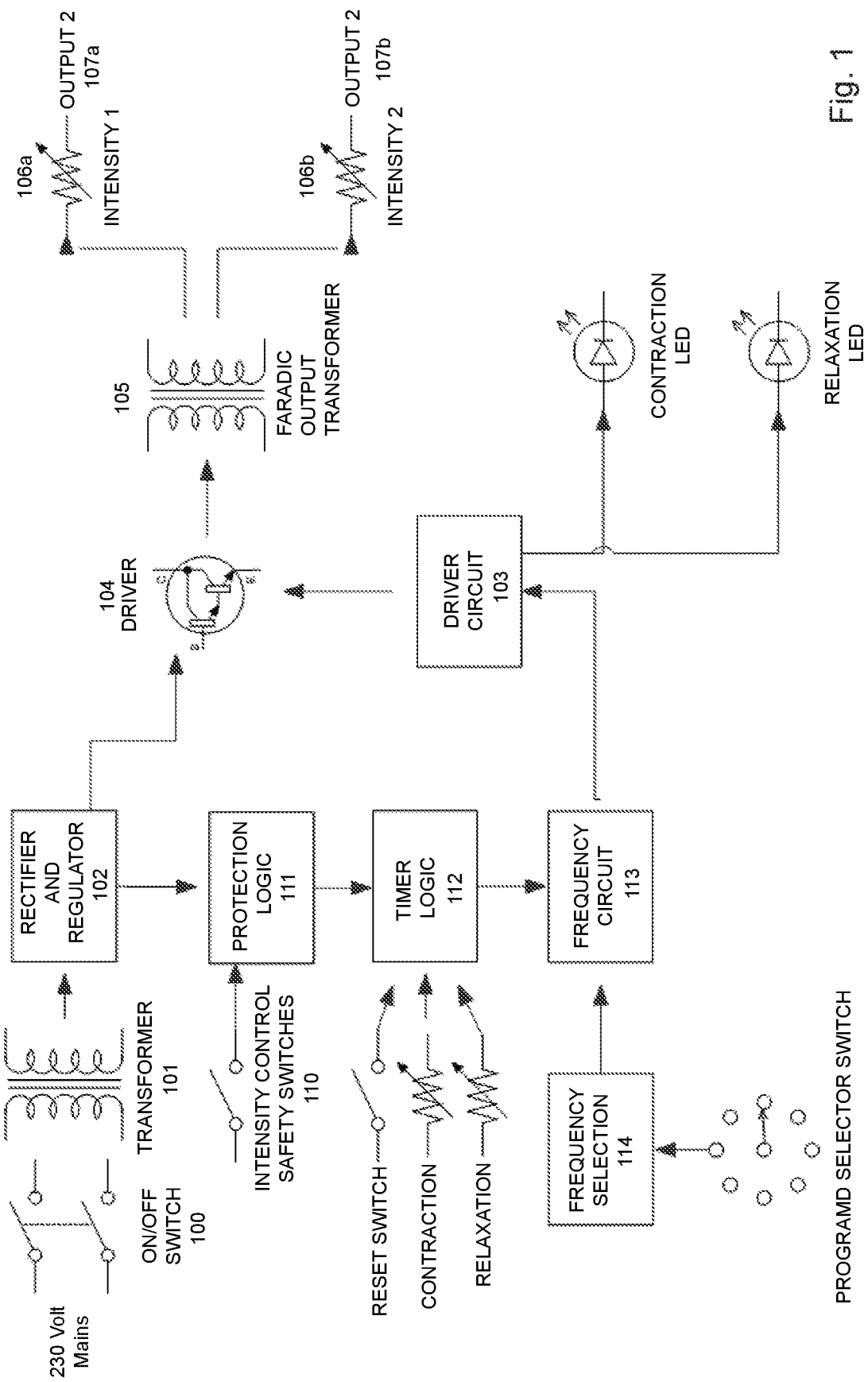
FIG. 1 shows a schematic circuit diagram of the specific embodiment of the generator of the present invention.

FIG. 1 shows a schematic circuit diagram of the specific embodiment of the generator of the present invention. In one preferred embodiment of the invention, the generator is connected electrically to a mains power source via an on/off switch 100. The AC current is passed to a transformer 101 and then to a rectifier 102. The AC current is rectified by the rectifier 102 into a DC current in the range of 1 to 5 mA and preferably 1 to 4 mA and in the range of 9-50V, preferably 9-40V. The rectifier 102 is connected to a protection logic module 111 which would switch off the device via an intensity control safety switch 110, if the intensity and/or the frequency of the generated current exceeds a predefined safety threshold, thereby providing the protection for the subject to be treated. The protection logic module 111 is connected to a timer logic module 112 for setting the time duration in which the contraction phase and the relaxation phase are implemented, respectively. The timer logic module 112 is then connected to a frequency circuit 113 and frequency selector 114 for selecting a proper frequency of the required current which is then provided as an output pulsed current transmitted to the electrical stimulation applicator 2 through a driver circuit 103, comprising a driver 104 (for example IC model nos. CD4069UBE or TLC556CN) and a Faradic output transformer 105. FIG. 1 further shows that the generator comprises at least two outputs (107a, 107b) of the same or different intensity, wherein the intensity of the output electrical stimulation at first output 107a and the second output 107b is controlled by a first intensity adjustment member 106a and a second intensity adjustment member 106b, respectively. It would be within the ability of a person skilled in the art that one output or more than two outputs of various current intensities are possible.

The generator may be operable to supply the electrical current at a frequency substantially in the range of 70 to 150 Hz, and preferably in the range of 80 to 120 Hz and with a pulse duration in the range of 50 to 200 μs, and preferably in the range of 100 to 180 μs.

The non-invasive device of the invention can repeatedly apply the desirable current to tissue at set frequency and intensity and allows for adjustment of frequency and intensity of the current.

Another aspect of the invention is to provide a probe unit 1 configured to be positioned externally and directly on target body surface of the vulvar tissues and/or the pelvic floor muscle so as to transmit an electrical stimulation to the vulvar tissues and/or the pelvic floor muscle. FIGS. 2 to 5 of the accompanying drawings show various embodiments of the probe units suitable for positioning externally and directly on target body surface of the vulvar tissues and pelvic floor muscle. According to the invention, the probe unit 1 may be provided in many different shapes or configurations adapted to fit onto the target body surface of the vulvar tissues and pelvic floor muscle.

Figure 2:
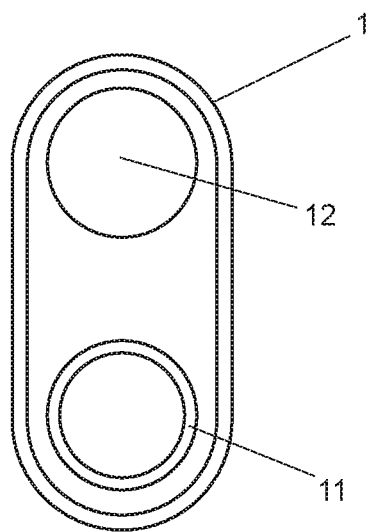
FIG. 2 shows in plan view a probe unit according to a specific embodiment of the present invention.

FIG. 2 shows in plan view a probe unit according to the first embodiment of the probe unit 1. The probe unit 1 is configured to have a rectangular shape with rounded edges and comprises one negative electrode 11 and one positive electrode 12 disposed opposite with each other in a length direction of the rectangular shape. The rectangular probe unit is sized and shaped such that it can be fitted on and around the surface of labia majora of vulva, labia minora of vulva, clitoris, external urethral sphincter muscle of vulva, vaginal orifice, perineum, or anus for stimulating the vulvar tissues and/or the pelvic floor muscle of these areas.

Figure 3:
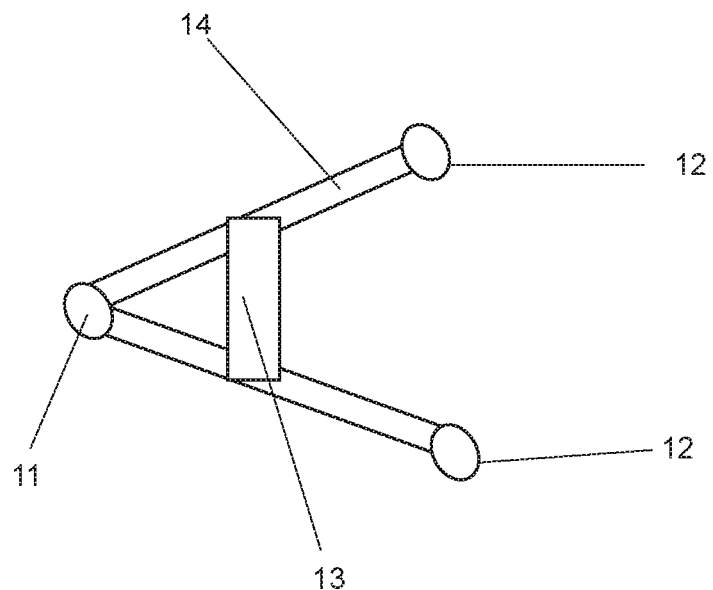
FIG. 3 shows in plan view a probe unit according to a further specific embodiment of the present invention.

A second embodiment of the probe unit 1 as shown in FIG. 3, is of a "V" shape with two ribs 14 extending from a common negative electrode 11. The probe unit 1 of FIG. 3 includes two positive electrodes 12 with each located at a free end of each of the ribs. The probe unit further includes a handle 13 connecting the two ribs 14. The handle 13 is arranged for easy grasp of the probe unit 1.

Figure 4:
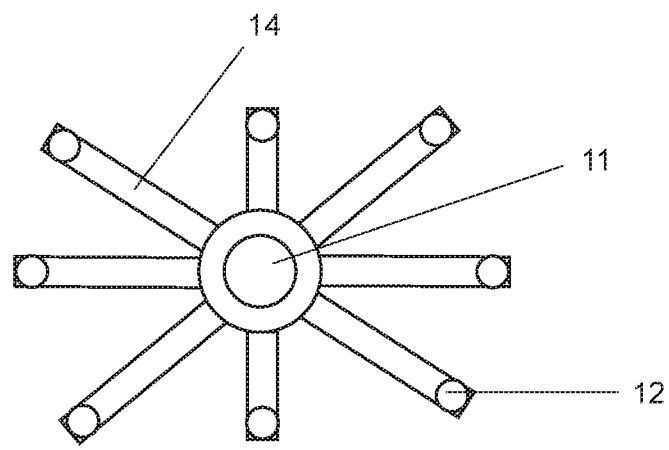
FIG. 4 shows in plan view a probe unit according to another specific embodiment of the present invention.

Referring to FIG. 4, a third embodiment of the probe unit 1 includes a negative electrode 11 with eight equally spaced ribs 14 extending radially from the common negative electrode 11, forming a shape of a "spider". The probe unit 1 further includes eight positive electrodes 12 with each located at a free end of each of the ribs 14.

Figure 5:
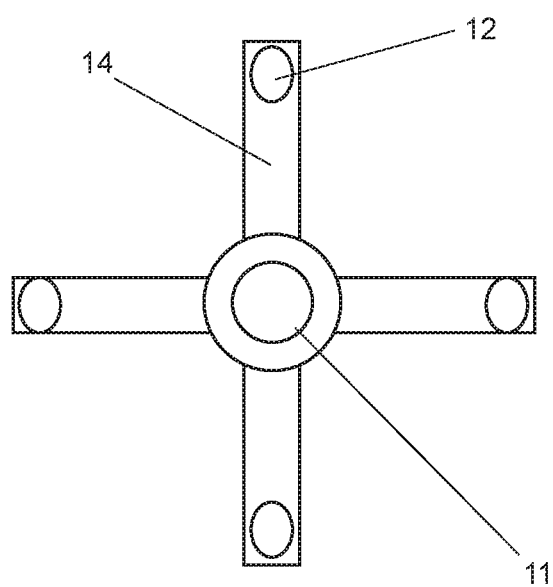
FIG. 5 shows in plan view a probe unit according to yet another specific embodiment of the present invention.

Referring to FIG. 5, a fourth embodiment of the probe unit 1 includes a negative electrode 11 with four equally spaced ribs 14 extending radially from the common negative electrode 11, forming a shape of a "cross". The probe unit 1 further includes four positive electrodes 12 with each located at a free end of each of the ribs 14.

It can be understood by those skilled in the art that the probe unit can include any numbers of ribs and positive electrodes, without being limited by the examples described. All the probe units are sized and shaped such that it can be fitted on and around the target body surface of the vulvar tissues and the pelvic floor muscle, such as, but not limited to, the surface of labia majora of vulva, labia minora of vulva, clitoris, external urethral sphincter muscle of vulva, vaginal orifice, perineum, or anus for stimulating the vulvar tissues and/or the pelvic floor muscle of these areas. The probe unit is also sized and shaped to concentrate current density on target muscles for better treatment effects and to allow local concentration of current with less chance of stimulation crossover into nearby muscles which are not targeted. Depending on the actual needs and/or the conditions of subjects and/or muscles to be targeted, probe units of different sizes and shapes may be used in order to better fit onto the sites and provide better treatment effects.

Figure 6:
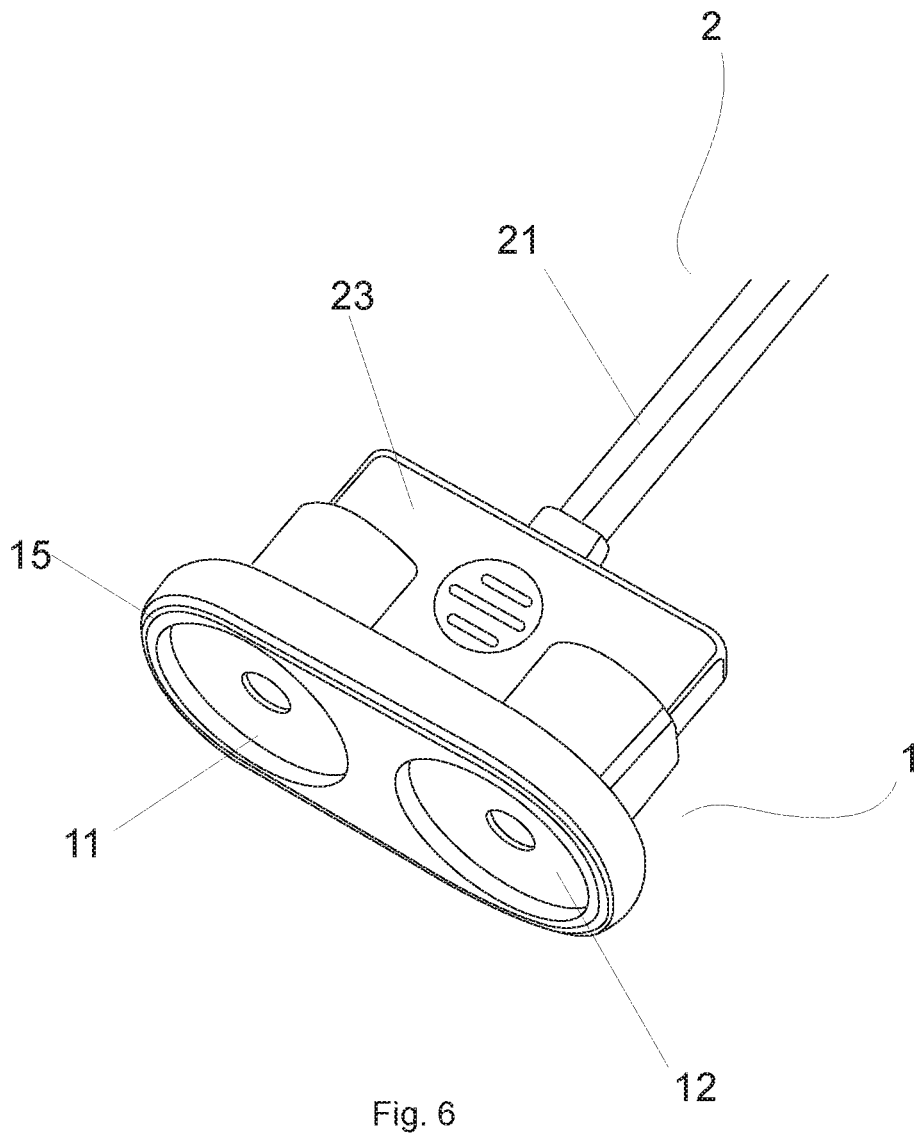
FIG. 6 is a perspective view of a probe unit as shown in FIG. 2 in connection with an electrical stimulation applicator.

Any of the above probe units may be disposable for hygiene and to prevent cross-contamination between patients. Moreover, all the probe units have a simple structure which are easy and economical for mass production. Furthermore, the probe unit further includes an anti-skid member on the surface of the probe unit in contact with the body surface of the patient to ensure the probe unit stays on the target muscle site during treatment. The anti-skid member can be a ridge 15 formed around the peripheral edge of the probe unit as shown in FIG. 6 or any other anti-skid patterns known in the art. One skilled in the art would appreciate that the anti-skid member can be any means that would prevent skidding or sliding of the probe unit during operation, for example, the probe unit may also include a non-slip sole made of soft plastic material.

Figure 7:
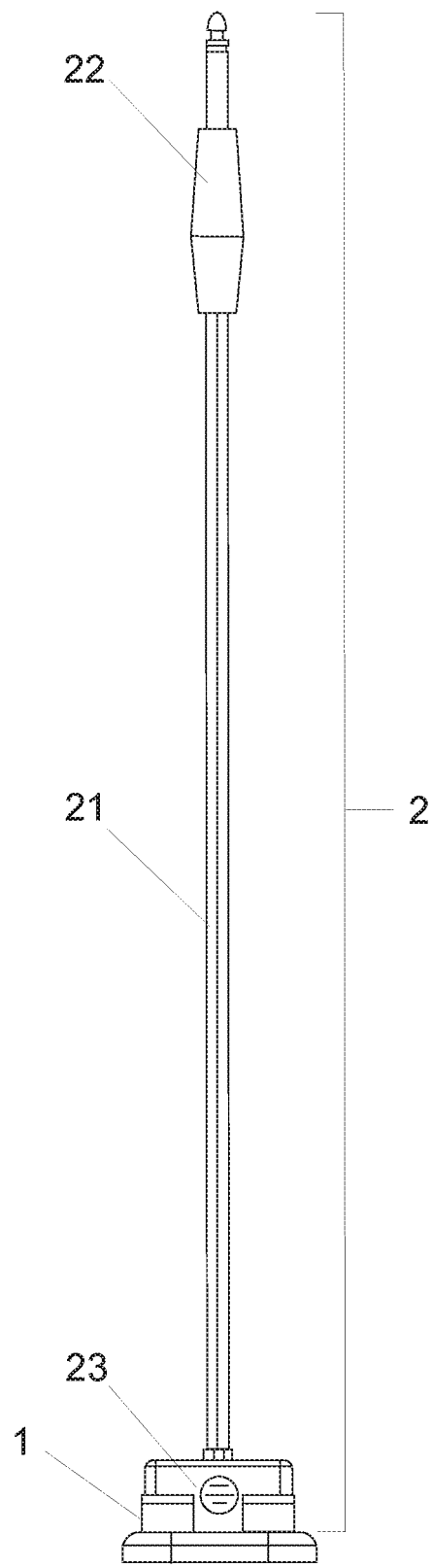
FIG. 7 is a front elevation view of an electrical stimulation applicator according to a specific embodiment of the present invention.
Figure 8A:
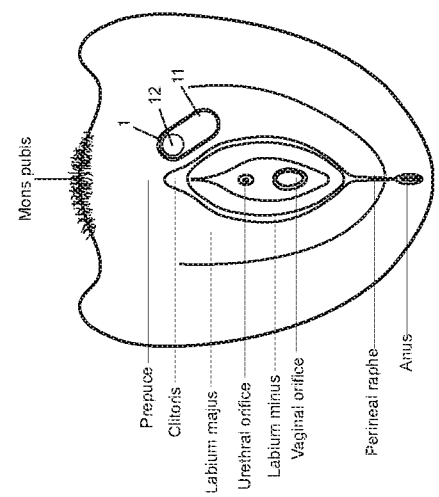
FIG. 8A-8F show ways for positioning the probe unit of FIG. 2 on a target body surface for improving the firmness and elasticity of labia majora.
Figure 8B:
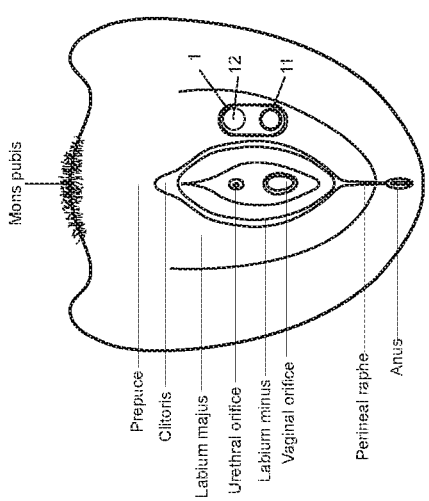
Figure 8C:
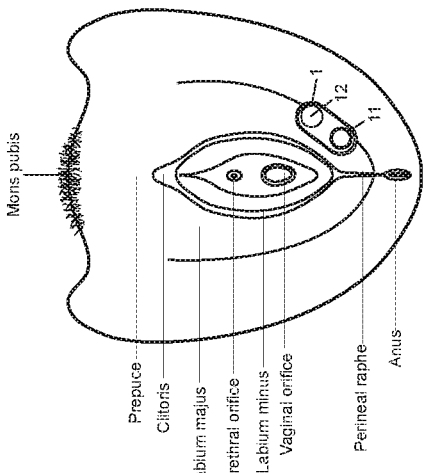
Figure 8D:
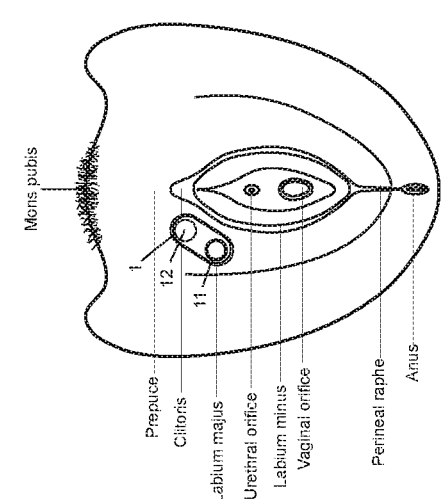
Figure 8E:
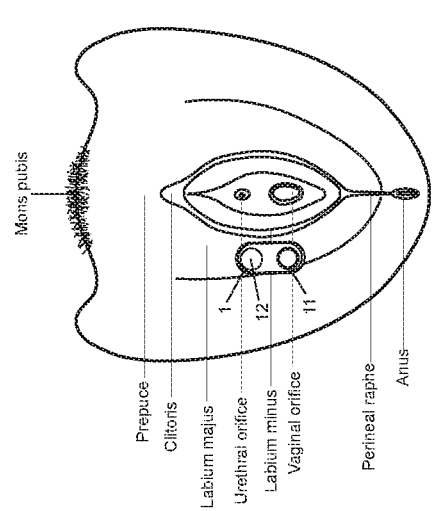
Figure 8F:
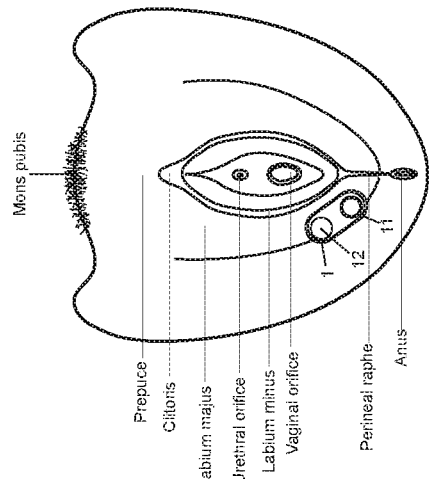

FIG. 6 shows a perspective view of a probe unit as shown in FIG. 2 in connection with an electrical stimulation applicator. The probe unit 1 is detachably connected to the electrical stimulation applicator 2 at its distal end. The distal end of the electrical stimulation applicator 2 can be configured as a female plug 23 for receiving the probe unit 1. The probe unit 1 can be removed or replaced easily by hand to facilitate change of different types of probe unit 1 for stimulating different target muscles during treatment. As shown in FIGS. 6 and 7 of the accompanying drawings, the electrical stimulation applicator 2 further comprises a cord/cable 21 for connecting the probe unit 1 to the generator. The electrical stimulation applicator 2 is plugged into the generator at its proximal end which may be configured as a male plug 22 as shown in FIG. 7.

The probe unit 1 of the present invention allows effective transmission of the electrical stimulation current onto the target muscles. In addition, conventionally, the positive electrodes and negative electrodes are disposed on separate units and it is often difficult for the operator or user to handle two or more electrodes at once for placing them onto the target muscles. In contrast, the negative electrode and one or more positive electrodes of the present invention are disposed on the same probe unit, thereby allowing the operator or user to handle the probe unit with ease or even with one hand.

Moreover, the shape of the negative electrode 11 and positive electrodes 12 can be a circle, ellipse, oval, or any other shape as long as it can transmit the current to a desired surface in a non-invasive manner. In many instances, the electrodes are a substantially spherical or semi-spherical member adapted for engagement with and fitting onto the target muscle sites in the pelvic floor. The probe unit can be fabricated from an electrically conductive material.

When in use for stimulating the vulvar tissues and/or the pelvic floor muscle for treating and improving dysfunction or disorders associated with pelvic floor, the electrical stimulation applicator 2 comprising the probe unit 1 is placed externally and directly onto a target body surface where the vulvar tissues and/or the pelvic floor muscles are located. The generator will be switched on to generate an electrical stimulation current with a predetermined intensity of milliampere and at a desirable frequency. The electrical stimulation current will be transmitted to the probe unit for application of an electrical stimulation to the vulvar tissues and/or pelvic floor muscle. According to the invention, at least one treatment cycle is applied, and each treatment cycle consisting of a contraction phase where the electrical stimulation is applied to the target vulvar tissues and/or the target pelvic floor muscle for a first period of time and a relaxation phase where no electrical stimulation is applied to the target vulvar tissues and/or the target pelvic floor muscle for a second period of time.

For effective stimulation of the vulvar tissues and/or pelvic floor muscles, the intensity of the electrical stimulation at the contraction phase is in the range of 1 to 5 mA, preferably in the range of 1.0 to 4 mA; and the voltage is in the range of 9 to 50 V, preferably in the range of 9 to 40 V; and the frequency of the electrical stimulation at the contraction phase is in the range of 70 to 150 Hz, and preferably in the range of 80 to 120 Hz and a pulse duration in the range of 50 to 200 µs, and preferably in the range of 100 to180 µs; and wherein the contraction phase lasts for 2 to 5 seconds, preferably 3 to 5 seconds; and more preferably 4 seconds. Further, the relaxation phase of the treatment cycle lasts for 2 to 7 seconds, preferably 5 to 7 seconds, and more preferably 6 seconds. Depending on the actual needs and/or the conditions of subjects, a plurality of treatment cycles may be applied.

Apart from the intensity, frequency, pulse duration of the electrical stimulation, placement of the electrodes of the present invention are also carefully designed in order to ensure muscle response and effective treatment. In particular, the probe unit is placed directly on or around the body surface of the following selected from a group consisting of labia majora of vulva, clitoris of vulva, external urethral sphincter muscle of vulva, vaginal orifice and labia minora of vulva, perineum, and anus.

FIG. 8A-8F show ways for positioning the probe unit of the first embodiment (FIG. 2) on a subject's body surface for improving the firmness and elasticity of labia majora. The rectangular probe unit is directly placed on and around the surface of labia majora of vulva, and at least one treatment cycle, which includes an electrical stimulation with a frequency of 100-120 Hz, current intensity of 1.0 mA-3.5 mA, a voltage of 9-32 V, a pulse duration of 100-140 µs and a contraction time of 3-5 s and a relaxation time of 5-7s, is applied to the body surface, thereby improving the firmness and elasticity of labia majora. In trial, a labia majora and labia minora with atrophic and sagging appearance are treated by placing the rectangular probe unit on and around the surface of labia majora of vulva for 30 minutes with an electrical stimulation with the parameters mentioned above. After 30 minutes of treatment, the firmness and elasticity of labia majora and labia minora are obviously improved. Further, the blood circulation and skin texture of vulva are also improved.

FIG. 9A-9F show ways for positioning the probe unit of the first embodiment on a subject's body surface for improving the firmness and elasticity of labia minora. The rectangular probe unit is directly placed on and around the surface of labia minora of vulva. In this embodiment, the treatment cycle, which includes an electrical stimulation with a frequency of 100-120 Hz, a current intensity of 1.0 mA-3.0 mA, a voltage of 9-28 V, a pulse duration of 100-140 µs and a contraction time of 3-5 s and a relaxation time of 5-7 s, is applied to the body surface, thereby improving the firmness and elasticity of labia minora. In another trial, a 52 years old woman suffered from labia minora atrophy with fusion problems and was treated for 30 minutes per week for 4 consecutive weeks with the abovementioned probe unit, positioning of the probe unit and parameters. After the first 30-minute treatment, the blood circulation and the firmness of the labia minora has obviously improved. And at the end of the fourth treatment after being treated for four consecutive weeks, the firmness and elasticity of labia minora have further improved and the blood circulation and skin texture of vulva have also improved.

Figure 10:
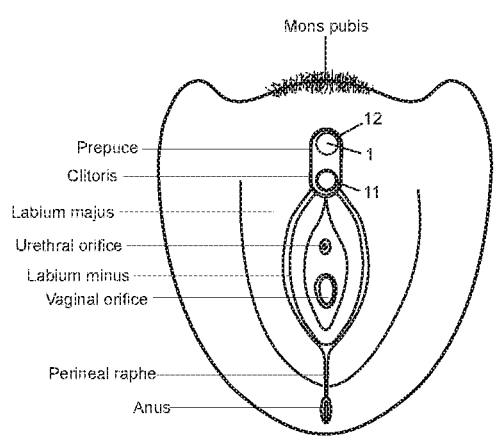
FIG. 10 shows way for positioning the probe unit of FIG. 2 on a target body surface for improving the strength, blood circulation and functionality of clitoris.

FIG. 10 shows way for positioning the probe unit of the first embodiment on a subject's body surface for improving the strength, blood circulation and functionality of clitoris. The rectangular probe unit is directly placed on and around the surface of clitoris of vulva, and at least one treatment cycle, which includes an electrical stimulation with a frequency of 100-120 Hz, a current intensity of 1.0 mA-2.2 mA, a voltage of 9-20 V, a pulse duration of 100-140 µs and a contraction time of 3-5 s and a relaxation time of 5-7 s, is applied to the body surface, thereby improving the strength, blood circulation and functionality of clitoris. It is found effective for alleviation of sexual dysfunctions. In trial, a 36 years old woman with clitoral atrophy and dryness was treated by placing the electrode of the rectangular probe unit directly on and around the surface of clitoris of vulva to apply an electrical stimulation with the abovementioned parameters. It has been found that after a 20-minute treatment, both clitoris and its hood were moisturized and texture of tissue was more moisturized and rejuvenated.

Figure 11:
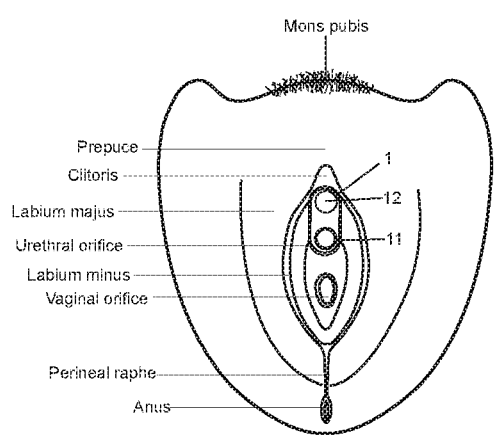
FIG. 11 shows way for positioning the probe unit of FIG. 2 on a target body surface for improving urinary incontinence.

FIG. 11 shows way for positioning the probe unit of the first embodiment on a subject's body surface for improving the strength and functionality of external urethral sphincter muscle. The rectangular probe unit is directly placed on and around the surface of external urethral sphincter muscle of vulva, and at least one treatment cycle, which includes an electrical stimulation with a frequency of 100-120 Hz, a current intensity of 1.0 mA-2.2 mA, a voltage of 9-20 V, a pulse duration of 100-140 µs and a contraction time of 3-5 s and a relaxation time of 5-7 s is applied to the body surface, thereby improving the strength and functionality of external urethral sphincter muscle. It is found effective for stimulating the nerve and improving urinary incontinence. In another trial, a 30+ years old woman suffered from stress urinary incontinence (SUI) after vaginal delivery, in particular, the external urethral sphincter muscle and the urethral meatus were loose and the urethral meatus was also dilated. She was treated by placing the negative electrode of the rectangular probe unit directly on and around the surface of external urethral sphincter muscle of vulva to apply an electrical stimulation with the parameters as stated above. After a 20-minute treatment, the urethral meatus was smaller than before and SUI was improved.

Figure 12:
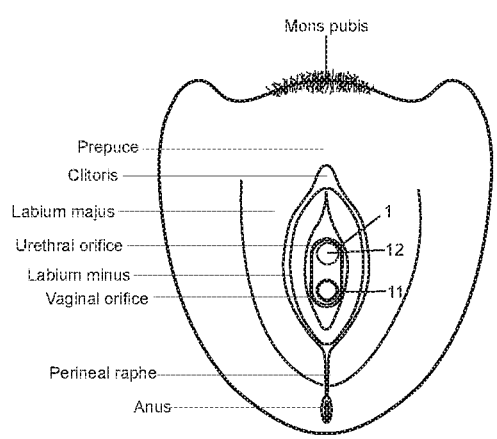
FIG. 12 shows way for positioning the probe unit of FIG. 2 on a target body surface for improving the firmness and elasticity of vaginal orifice and the bottom part of labia minora.

FIG. 12 shows way for positioning the probe unit of the first embodiment on a subject's body surface for improving the firmness and elasticity of vaginal orifice and the bottom part of labia minora. The rectangular probe unit is directly placed on and around the surface of vaginal orifice and labia minora of vulva, and at least one treatment cycle, which includes an electrical stimulation with a frequency of 100-120 Hz, a current intensity of 1.0 mA-2.2 mA, a voltage of 9-20 V, a pulse duration of 100-140 µs and a contraction time of 3-5 s and a relaxation time of 5-7 s, is applied to the body surface, thereby improving the firmness and elasticity of vaginal orifice and the bottom part of labia minora. In trial, a 36 years old woman with loose vaginal meatus was treated by placing a rectangular probe unit directly on and around the surface of vaginal orifice and labia minora of vulva to apply an electrical stimulation with parameters as described above. Ager being treated for 30 minutes for a first time and after 7 days, a second time for another 30 minutes, the firmness and elasticity of the vaginal meatus and the bottom part of labia minora were obviously improved.

Figure 13A:
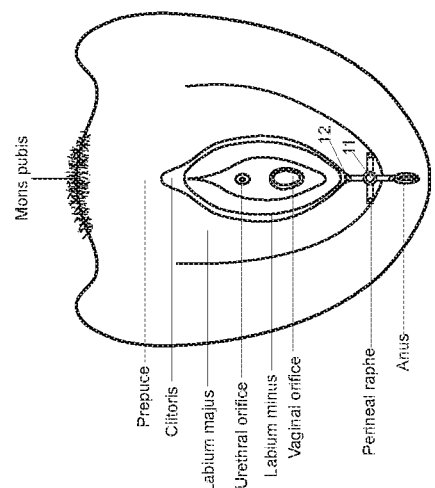
FIG. 13A-13B show ways for positioning the probe unit of FIG. 5 on a target body surface for improving the firmness and elasticity of perineum.
Figure 13B:
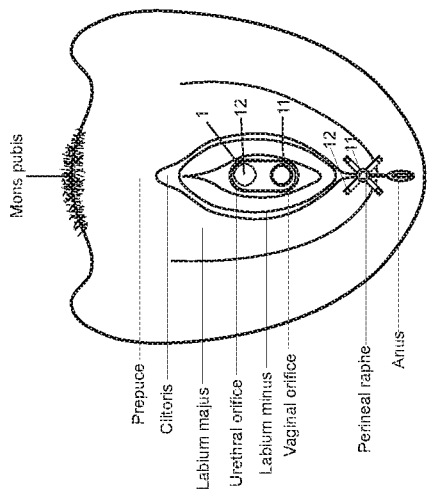
Figure 14A:
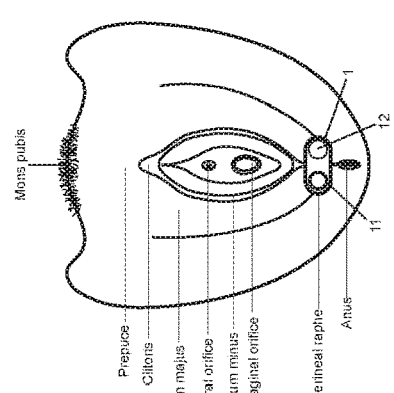
FIG. 14A-14H show ways for positioning the probe unit of FIG. 2 on a target body surface for improving the firmness and elasticity of perineum.
Figure 14B:
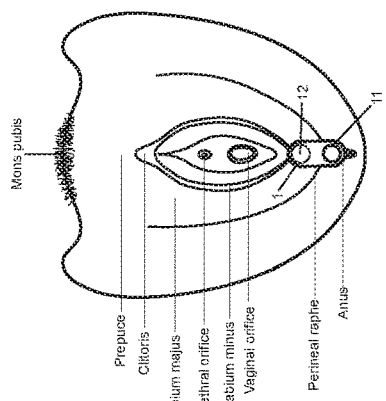
Figure 14C:
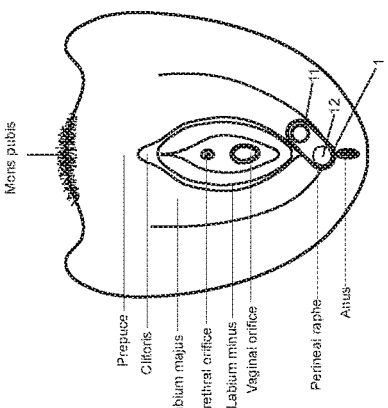
Figure 14D:
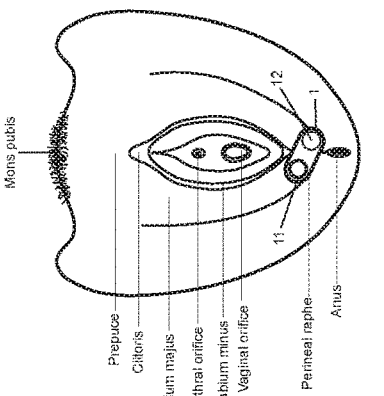
Figure 14E:
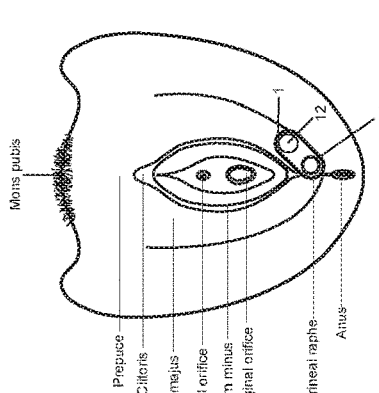
Figure 14F:
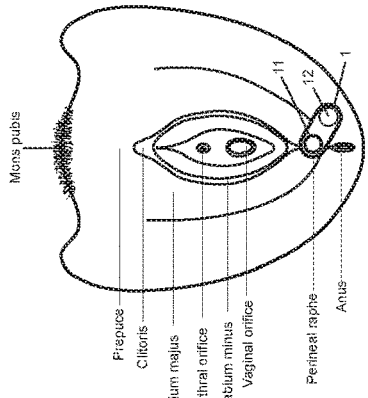
Figure 14G:
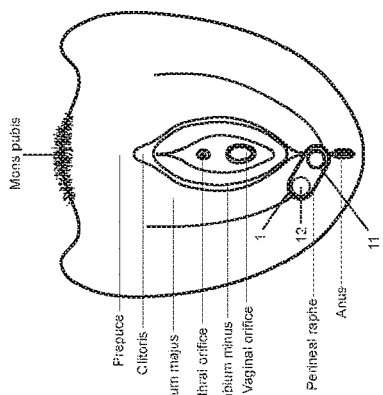
Figure 14H:
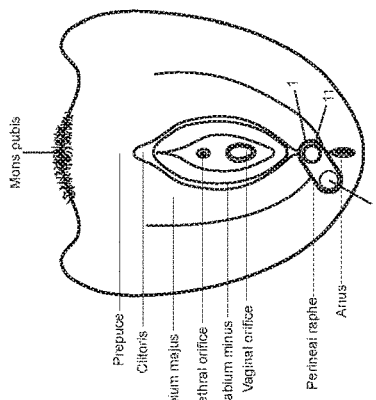

FIGS. 13A-13B show ways for positioning the probe unit of the fourth embodiment (FIG. 5) on a subject's body surface for improving the firmness and elasticity of perineum. The 'cross' probe unit with four ribs extending from a common negative electrode is directly placed on and around the surface of perineum, and at least one treatment cycle, which includes an electrical stimulation with a frequency of 80-100 Hz, a current intensity of 1.0 mA-4.0 mA, a voltage of 9-40 V, a pulse duration of 140-180 µs and a contraction time of 3-5 s and a relaxation time of 5-7 s, is applied to the body surface, thereby improving the firmness and elasticity of perineum. It is found effective for reducing the sexual dysfunction and strengthening the support to pelvic floor.

Alternatively, FIGS. 14A-14H show ways for positioning the probe unit of the first embodiment on a subject's body surface for improving the firmness and elasticity of perineum. The rectangular probe unit is directly placed on and around the surface of perineum, and at least one treatment cycle, which includes an electrical stimulation with a frequency of 80-100 Hz, a current intensity of 1.0 mA-4.0 mA, a voltage of 9-40 V, a pulse duration of 140-180 µs and a contraction time of 3-5 s and a relaxation time of 5-7 s is applied to the body surface, thereby improving the firmness and elasticity of perineum. It is found effective for alleviating the sexual dysfunction and strengthening and stabilizing the support to pelvic floor. In trial, the perineum of a 40-years old woman was suffered from poor blood circulation, dilated veins with sagging and dry appearance. She was treated by placing the rectangular probe unit directly on and around the surface of perineum to apply an electrical stimulation with the abovementioned parameters. After a 20-minute treatment, the blood circulation and skin texture of the perineum were obviously improved. Further, the blood vessels of the perineum has become firmer.

Figure 15:
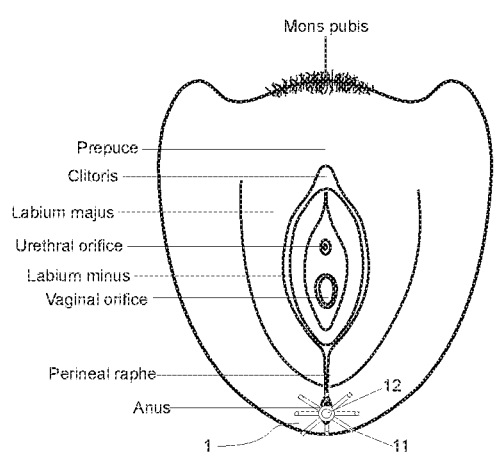
FIG. 15 shows way for positioning the probe unit of FIG. 4 on a target body surface for improving the strength, blood circulation and firmness of external anal sphincter muscle.

FIG. 15 shows way for positioning the probe unit of the third embodiment (FIG. 4) on a subject's body surface for improving the strength, blood circulation and firmness of external anal sphincter muscle. The probe unit with eight ribs extending from a common negative electrode is directly placed on and around the surface of anus, and at least one treatment cycle, which includes an electrical stimulation with a frequency of 80-100 Hz, a current intensity of 1.0 mA-4.0 mA, a voltage of 9-40 V, a pulse duration of 140-180 μs and a contraction time of 3-5 s and a relaxation time of 5-7 s is applied to the target body surface, thereby improving the strength, blood circulation and firmness of external anal sphincter muscle. It is found effective for alleviating the problems of external hemorrhoids constipation and anal incontinence.

FIGS. 16A-16H show ways for positioning the probe unit of the second embodiment (FIG. 3) on a subject's body surface for improving the strength, blood circulation and firmness of external anal sphincter muscle. The "V" shaped probe unit is directly placed on and around the surface of anus, and at least one treatment cycle, which includes an electrical stimulation with a frequency of 80-100 Hz, a current intensity of 1.0 mA-4.0 mA, a voltage of 9-40 V, a pulse duration of 140-180 μs and a contraction time of 3-5 s and a relaxation time of 5-7 s is applied to the target body surface, thereby improving the strength, blood circulation and firmness f external anal sphincter muscle. It is found effective for alleviating the problems of external hemorrhoids constipation and anal incontinence.

FIGS. 17A-17H show ways for positioning the probe unit of the first embodiment on a subject's body surface for improving the strength, blood circulation and firmness of external anal sphincter muscle. The rectangular probe unit is directly placed on and around the surface of anus, and at least one treatment cycle, which includes an electrical stimulation with a frequency of 80-100 Hz, a current intensity of 1.0 mA-4.0 mA, a pulse duration of 140-180 μs and a contraction time of 3-5 s and a relaxation time of 5-7 s is applied to the target body surface, thereby improving the strength, blood circulation and firmness of external anal sphincter muscle. It is found effective for alleviating the problems of external hemorrhoids constipation and anal incontinence. In trial, a 50+ years old woman suffered from a wrinkled perineum and external hemorrhoid was treated by placing the rectangular probe unit directly on and around the surface of anus to apply an electrical stimulation with the parameters as descripted above. She was treated for 20 minutes for 2 times. After the first 20-minute treatment, the external anal sphincter muscle and the perineum has become firmer. And after the second 20-minute treatment, the external hemorrhoid has significantly reduced. In yet another trial, a 60 years old woman with loose external anal sphincter muscle and external hemorrhoid was treated with the same probe unit and parameters as the above trial but for 18 times. The first 12 treatments were carried out weekly while the rest of the 6 treatments were carried out every 2 weeks. After the 18 treatments, the external anal sphincter muscle was significantly firmer, and the external hemorrhoid has disappeared.

The below table shows the effectiveness of the treatments for different conditions after undergoing a first 30-minute treatment. In all the trials, the subjects were treated for 30 minutes with the probe unit and parameters as stated above for each of the conditions. The treatments are considered as effective when there are clear signs of improvement to the conditions. For example, a significant and noticeable improvement in the firmness and elasticity of labia majora and labia minora for the treatment of labia majora and labia minora atrophy; a significant and noticeable improvement to the dryness and appearance of the clitoris for the treatment of clitoral atrophy and dryness, a significant and noticeable improvement in urinary incontinence for the treatment of stress urinary incontinence, a significant and noticeable improvement in the firmness and elasticity of the vaginal meatus and the bottom part of labia minora for the treatment for loose vaginal meatus; a significant and noticeable improvement in the firmness, elasticity and blood circulation of perineum for the treatment on perineum; and a significant and noticeable improvement in the firmness of external anal sphincter muscle as well as improvement in external hemorrhoids constipation and anal incontinence for the treatment for external hemorrhoids constipation and anal incontinence.

TABLE 1

The effectiveness of the treatments for different conditions after undergoing a first 30-minute treatment

| Type of conditions | No. of Trials | No. of Trials found effective after first 30-min treatment | Percentage of effectiveness (%) |
|---|---|---|---|
| labia majora atrophy | 40 | 38 | 95 |
| labia minora atrophy | 38 | 35 | 92 |
| clitoral atrophy and dryness | 36 | 34 | 94 |
| stress urinary incontinence (SUI) | 20 | 16 | 80 |
| loose vaginal meatus | 25 | 21 | 84 |
| perineum atrophy and dryness | 25 | 20 | 80 |
| external hemorrhoids constipation and anal incontinence | 25 | 19 | 76 |

As can be seen from the above table, about 76% to 95% of the treatments applied for different conditions are found to be effective after a first 30-minute treatment. Those were less effective after the first treatment were usually with a more severe conditions and were found effective after undergoing several treatments, for example after three to four 30-minute treatments.

As can be seen, the probe unit 1 of the present invention is placed onto the target body surface and the probe unit is sized and shaped to fit onto the target body surface and allow focused transmission of the required current to a designated muscle or tissue surface. Furthermore, the current intensity of the electrical stimulation is in milliampere range to reduce discomfort and pain as well as to ensure effectiveness of the treatment. The non-invasive device of the invention can achieve various treatment effects on the pelvic floor in a substantially non-abrasive manner without causing any significant damage to the muscle and tissue.

It should be appreciated that the placement of the probe unit is not limited to the disclosed embodiments. In particular, more than one probe units can be placed on the same or different part of the target body surface on or around the vulvar tissues and/or the pelvic floor muscle for synergistic or simultaneous stimulation and treatment.

While the present invention is described in connection with what is presently considered to be the most practical and preferred embodiment, it should be appreciated that the invention is not limited to the disclosed embodiment, and is intended to cover various modifications and equivalent arrangements included within the spirit and scope of the claims. Modifications and variations in the present invention may be made without departing from the novel aspects of the invention as defined in the claims, and this application is limited only by the scope of the claims.

What is claimed is:

1. A non-invasive device for stimulating vulvar tissues and/or pelvic floor muscles for treating and improving dysfunction or disorders associated with the pelvic floor, said device comprises:
   a generator configured to generate a current suitable for treatment with a predetermined intensity of milliamperes at a desirable frequency; said generator comprising a control unit configured to control the generation of the current;
   at least one electrical stimulation applicator comprising a distal end electrically connected to the generator and configured to receive the current generated by the generator, and a proximal end electrically connected to a probe unit configured to transmit the current to a target body surface of the vulvar tissues and/or the pelvic floor muscle for application of an electrical stimulation; wherein the probe unit comprises a negative electrode and at least one positive electrode and the probe unit is shaped for externally, movably and directly positioning on the target body surface of the vulvar tissues and/or the pelvic floor muscle;
   wherein the control unit of the generator is programmed to deliver at least one treatment cycle consisting of
      a contraction phase where the probe unit moves around the external body surface of the target vulvar tissues and/or the target pelvic floor muscle so that the electrical stimulation is applied to the target vulvar tissues and/or the target pelvic floor muscle for a first period of time; and
      a relaxation phase where no electrical stimulation is applied to the target vulvar tissues and/or the target pelvic floor muscle for a second period of time,
   wherein the control unit of the generator comprises a frequency adjustment module for adjusting the frequency of the generated current, and a timer logic module configured to control a length of the contraction phase and a length of the relaxation phase.

2. The device according to claim 1, wherein the frequency adjustment module comprises a frequency circuit and a frequency selector configured to select the frequency of the current.

3. The device according to claim 1, wherein the control unit of the generator further comprises a protection logic module configured to switch off the device if any one of the frequency or the intensity of the generated current exceeds a predefined safety threshold.

4. The device according to claim 1, wherein the intensity of the electrical stimulation at the contraction phase is in the range of 1.0-5.0 mA, and the frequency of the electrical stimulation at the contraction phase is in the range of 70-150 Hz, and wherein the contraction phase lasts for 2 to 5 seconds.

5. The device according to claim 1, wherein the electrical stimulation at the contraction phase has a pulse duration in the range of 50 to 200 μs.

6. The device according to claim 1, wherein the relaxation phase lasts for 2 to 7 seconds.

7. The device according to claim 1 wherein the probe unit is shaped for positioning on or around the body surface of the following selected from a group consisting of labia majora and labia minora of vulva, clitoris of vulva, external urethral sphincter muscle of vulva, vaginal orifice, perineum, and anus for stimulating the vulvar tissues and/or the pelvic floor muscle in the region.

8. The device according to claim 1 wherein the probe unit is a disposable probe unit detachably attached to the proximal end of the electrical stimulation applicator.

9. The device according to claim 1 wherein the probe unit comprises 1 to 8 positive electrodes.

10. The device according to claim 1 wherein the probe unit is configured to have a rectangular shape and includes one negative electrode and one positive electrode opposite with each other in a length direction of the rectangular shape.

11. The device according to claim 10 wherein the probe unit is configured to have a "V" shape with two ribs extending radially from the negative electrode and the probe unit comprises two positive electrodes with each located at a free end of each of the ribs.

12. The device according to claim 10 wherein the probe unit comprises four equally spaced ribs extending radially from the negative electrode and the probe unit comprise four positive electrodes with each located at a free end of each of the ribs.

13. The device according to claim 10 wherein the probe unit comprises eight equally spaced ribs extending radially from the negative electrode and the probe unit comprises eight positive electrodes with each located at a free end of each of the ribs.

14. The device according to claim 10, wherein the probe unit has a rectangular shape with rounded edges.

15. The device according to claim 1 wherein the probe unit comprises a plurality of ribs extending radially from the negative electrode, wherein one positive electrode is located at a free end of each of the ribs.

16. The device according to claim 15, wherein the probe unit further comprises a handle connecting the two ribs.

17. The device according to claim 1 wherein the probe unit further comprises an anti-skid member on the surface of the probe unit in contact with the target body surface.

18. A method for application of electrical stimulation to stimulate vulvar tissues and/or pelvic floor muscles for treating dysfunction or disorders associated with the pelvic floor, the method comprising the steps of:
   placing at least one electrical stimulation applicator comprising a probe unit externally and directly onto a target body surface where the vulvar tissues and/or the pelvic floor muscles are located, wherein the probe unit which is movably in contact with the target body surface comprises one negative electrode and at least one positive electrode;
   generating a current suitable for treatment with a predetermined intensity of milliamperes and at a desirable frequency by a generator and providing the current to the probe unit for application of the electrical stimulation to the vulvar tissues and/or the pelvic floor muscle;
   wherein the method further comprises at least one treatment cycle consisting of a contraction phase where the probe unit moves around the external body surface of the target vulvar tissues and/or the target pelvic floor muscle so that the electrical stimulation is applied to the target vulvar tissues and/or the target pelvic floor muscle for a first period of time and a relaxation phase where no electrical stimulation is applied to the target vulvar tissues and/or the target pelvic floor muscle for a second period of time.

19. The method according to claim 18, wherein the probe unit is placed directly on or around the body surface of the following selected from a group consisting of labia majora and labia minora of vulva, clitoris of vulva, external urethral sphincter muscle of vulva, vaginal orifice, perineum, and anus.

\* \* \* \* \*